(12) United States Patent
Lakshminarayan et al.

(10) Patent No.: US 9,078,629 B2
(45) Date of Patent: Jul. 14, 2015

(54) DETECTING REGIME CHANGE IN STREAMING DATA

(75) Inventors: Choudur K. Lakshminarayan, Austin, TX (US); Evan Kriminger, Gainesville, FL (US); Jose C. Principe, Gainesville, FL (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 369 days.

(21) Appl. No.: 13/235,556

(22) Filed: Sep. 19, 2011

(65) Prior Publication Data
US 2013/0069786 A1    Mar. 21, 2013

(51) Int. Cl.
| | | |
|---|---|---|
| *A61B 5/00* | (2006.01) | |
| *G06K 9/00* | (2006.01) | |
| *A61B 5/0452* | (2006.01) | |

(52) U.S. Cl.
CPC .......... *A61B 5/7282* (2013.01); *G06K 9/00496* (2013.01); *A61B 5/0452* (2013.01)

(58) Field of Classification Search
CPC ..................... G06Q 10/06; G06F 17/18; G06F 11/07–11/20; G06F 11/3409; G01F 25/0007; G01F 1/74; A01G 25/16
USPC .............. 340/603, 606, 3.42, 3.43, 3.44, 679; 702/179–186, 44–55; 700/281–285; 116/112, 264; 73/1.16, 152.18, 152.29, 73/863.02
See application file for complete search history.

(56) References Cited

U.S. PATENT DOCUMENTS

| | | | | |
|---|---|---|---|---|
| 2008/0033693 | A1* | 2/2008 | Andenna et al. | 702/179 |
| 2008/0082297 | A1* | 4/2008 | Lundeberg et al. | 702/183 |
| 2009/0300417 | A1* | 12/2009 | Bonissone et al. | 714/26 |
| 2011/0173482 | A1* | 7/2011 | Penton et al. | 714/2 |

OTHER PUBLICATIONS

V. Chandola, et. al., Anomaly Detection: A survey, ACM Computing Surveys, vol. 41, Issue 3, Jul. 2009, NY USA.*
S. J. Nowlan, et al., Evaluation of Adaptive Mixtures of Competing Experts, Proceedings of NIPS, 1990, pp. 774-780.
M. I. Jordan et al., Hierarchical Mistures of Experts and the EM Algorithm, AI Memo No. 1440, C.B.C.L. Memo No. 83, Aug. 6, 1993, MIT.
R. A Jacobs et al., Adaptive Mixtures of Local Experts (1991), Neural Computations, 3,9-87 (1991). MIT.
Y. H. Hu, et al., A Patient-Adaptive ECG Beat Classifier Using a Mixture of Experts Approach, IEEE Transactions on Biomedical Engineering, V. 44, No. 9, Sep. 1997, pp. 891-900.
C. Fancourt, Modeling segmentation and classification of nonlinear nonstationary time series, Nonlinear Dynamical Systems: Feedforward Neural Network Perspectives, c. 4, 2001.
E. Kriminger, et al. Modified Embedding for Multi-Regime Detection in Nonstationary Streaming Data, ICASSP, pp., May 2011.

(Continued)

*Primary Examiner* — Brian Zimmerman
*Assistant Examiner* — Laura Nguyen
(74) *Attorney, Agent, or Firm* — Trop, Pruner & Hu, P.C.

(57) ABSTRACT

Regime change in streaming data is detected. The streaming data is sent to a plurality of modules. Each module in the plurality of modules produces an association measure. The association measure is a measure of similarity between the streaming data and regime data associated with the module producing the association measure. A regime change in the streaming data is detected based on values of the association measures from the plurality of modules.

20 Claims, 4 Drawing Sheets

(56) References Cited

OTHER PUBLICATIONS

A. Agovic et al., "Anomaly detection in transportation corridors using manifold embedding," in 1st Int. Workshop on Knowledge Discovery from Sensor Data. 2007, ACM Press (10 pages).

A. Groth, "Visualization of coupling in time series by order recurrence plots," Physical Review E, vol. 72, pp. 046220, 2005 (8 pages).

A. Patcha and J. M. Park, "An overview of anomaly detection techniques: existing solutions and latest technological trends," Comput. Networks, vol. 51, No. 12, pp. 3448-3470, 2007.

Floris Takens, "Detecting strange attractors in turbulence," Lecture Notes in Mathematics, vol. 898, No. 1, pp. 366-381, 1981.

Ignacio Santamaria et al., "Generalized correlation function: definition, properties, and application to blind equalization," IEEE Transactions on Signal Processing, vol. 54, No. 6-1, pp. 2187-2197, 2006.

Ludmila I. Kuncheva et al., "Decision templates for multiple classifier fusion: an experimental comparison," Pattern Recognition, vol. 34, pp. 299-314, 2001.

Peter Grassberger and Itamar Procaccia, "Characterization of strange attractors," Phys. Rev. Lett., vol. 50, No. 5, pp. 346-349, Jan. 1983.

T. Sauer et al., "Embedology," Journal of Statistical Physics, vol. 65, No. 3-4, pp. 579-616, 1991.

Zoubin Ghahramani and Geoffrey E. Hinton, "Variational learning for switching state-space models," Neural Computation, vol. 12, pp. 963-996, 1998.

* cited by examiner

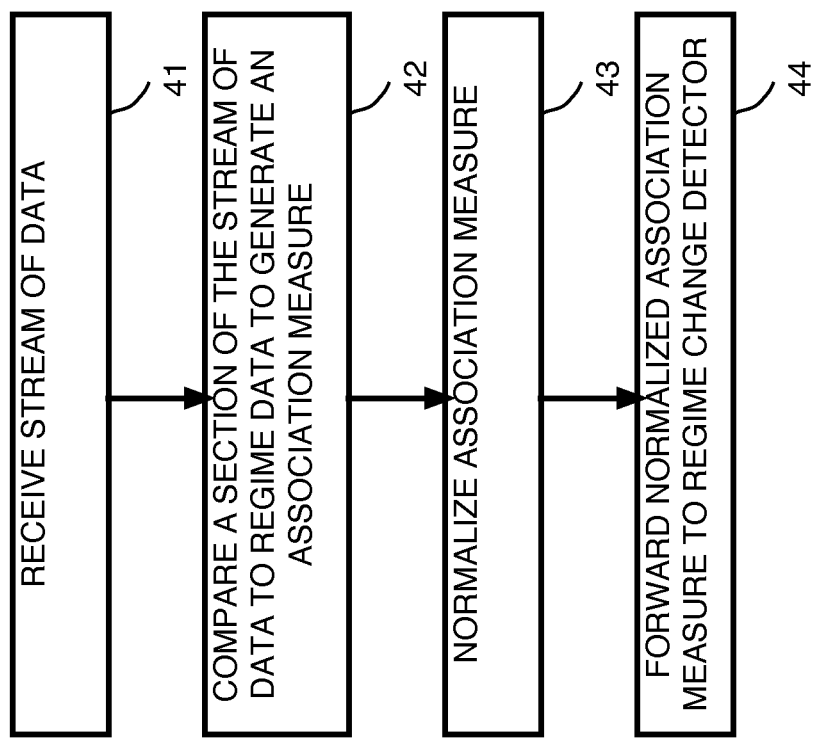

DETECTING REGIME CHANGE IN STREAMING DATA

BACKGROUND

Streaming data can be used to represent a wide variety of phenomena such as the price of a company stock over time, a rate of fluid flow through a pipe or a physical process within a human body. Streaming data may exhibit distinct patterns of behavior that may be detected, for example, by analyzing dynamical or statistical properties of the data. Streaming data with similar patterns of behavior may be categorized as being within a single regime.

The ability to categorize streaming data into regimes and to detect a change in the regime of streaming data can provide useful information, such as signaling an anomaly or abnormality in underlying phenomena represented by the streaming data. For example, a regime change in streaming data derived from stock price may provide a buy or a sell signal in a technical analysis system. A regime change in streaming data derived from rate of fluid flow through a pipe may indicate a significant event in a well that is the source of the fluid. A regime change in streaming data derived from an electrocardiogram may signal a significant cardiac event.

BRIEF DESCRIPTION OF DRAWINGS

FIG. 4 is a simplified flowchart that summarizes operation of a module in accordance with an implementation.

DETAILED DESCRIPTION

Regime change in streaming data is detected. What is meant by streaming data is a sequence of coherent signals that represent information. The streaming data may exhibit particular patterns of behavior. Patterns of behavior in the streaming data that are, for example, distinguished by similar dynamical and statistical properties can be construed as regimes. Transitions from one regime to another may indicate process anomalies and abnormalities in a process represented by the information.

In order to detect regime change, the streaming data is sent to a plurality of modules that are programs executable on a processor. Each module in the plurality of modules produces an association measure. The association measure is a measure of similarity between the streaming data and particular regime data associated with the module producing the association measure. The particular regime data, for example, consists of a selection of data that exhibits particular patterns of behavior distinguished by dynamical and statistical properties that are characteristic of a particular regime.

A regime change in the streaming data is detected based on values of the association measures from the plurality of modules. For example, the values of the association measures can be monitored to determine to which particular regime data the streaming data is most similar. When changes in the values of the association measures indicate there is a change in the identity of the particular regime data to which the streaming data is most similar, this indicates a regime change in the streaming data. For example, the association measures can be normalized to facilitate comparisons between association measures.

Figure 1:
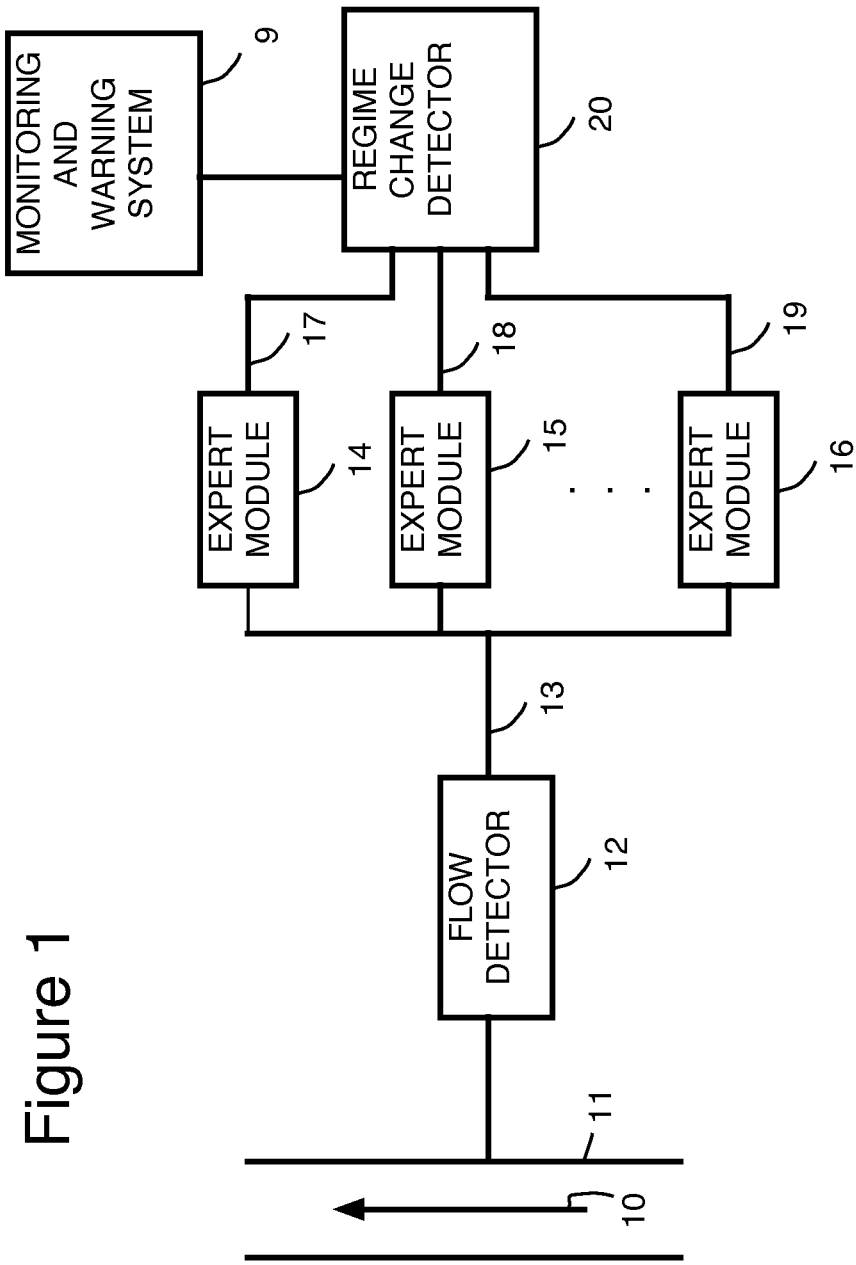
FIG. 1 is a simplified block diagram of a system that detects a regime change in streaming data derived from fluid flow in accordance with an implementation.

FIG. 1 is a simplified block diagram of a system that detects a regime change in streaming data derived from fluid flow. Arrow 10 represents fluid flow through a pipe 11. A flow detector 12 monitors fluid flow 10 and produces streaming data on line 13 that represents characteristics of fluid flow 10. For example the streaming data may be in the form of an analog signal or a digital signal. In parallel, the streaming data is received by a plurality of modules. The plurality of modules is represented in FIG. 1 by an expert module 14, an expert module 15 and an expert module 16. While FIG. 1 shows three modules, this is only exemplary as the number of modules may be as low as two and as high as the number of regimes to be detected.

Each module has associated with it regime data. The regime data associated with a module defines the characteristics of the regime for the module. Each module compares its regime data with the streaming data. Based on the comparison, the module generates an association measure. The association measure indicates how closely characteristics of the streaming data match characteristics of the regime data associated with the module.

A regime change detector 20 receives an association measure from each of the modules. This is illustrated in FIG. 1 by regime change detector 20 receiving an association measure from expert module 14 over line a 17. Regime change detector 20 receives an association measure from expert module 15 over a line 18. Regime change detector 20 receives an association measure from expert module 16 over a line 19.

As the modules receive the streaming data, regime change detector 20 monitors the association measures generated by the modules. Change detector 20 determines from the association measures which regime currently best fits the characteristics of the streaming data. For example, if a high value for an association measure indicates close correlation to regime data, then regime change detector 20 categorizes the streaming data as being in the regime associated with the module that produces the highest association measure. If a low value for an association measure indicates close correlation to regime data, then regime change detector 20 categorizes the streaming data as being in the regime associated with the module that produces the lowest association measure.

When the association measures indicate there is a change in which regime currently best fits the characteristics of the streaming data, regime change detector 20 detects there has been a regime change. Regime change detector 20 signals a monitoring and warning system 9 that a regime change has occurred. Based on the new regime, monitoring and warning system 9 takes an appropriate predetermined action.

Each module can calculate its association measure in a manner different than other modules calculate their association measures. For example, a feature is extracted from the regime data and compared to a looked for equivalent feature in the streaming data. For example, the feature may be particularly shaped oscillation peaks. Different modules may use different features to calculate their association measures.

Also, different modules may use different methodologies to calculate association measures. One module may calculate its association measure using Hamming distance. Another module may calculate its association measure based on Euclidean distance. Another module may utilize a likelihood ratio to calculate its association measure between the streaming data and regime data associated with the module. And so on.

When different modules use different methodologies to calculate association measures, it may be necessary to normalize the calculated association measures so that the association measure from each module can be accurately compared with each other.

For example, a normalized association value $Z_i$ can be calculated from a non-normalized association value $a_i$ for i=1, 2, ..., k, for each module i where k is the number of regimes. For example, such a calculation can use the mean $\mu_i$ and the standard deviation $\sigma_i$ from a sampling distribution of non-normalized association values generated by each module i, as set out in the following equation (1):

$$Z_i = \frac{a_i - \mu_i}{\sigma_i} \qquad \text{Equation (1)}$$

The regime data associated with expert modules 14, 15 and 16 can be obtained, for example, by monitoring data flow 10 under various conditions to produce training data. The training data can then be analyzed to determine if there are particular patterns or characteristics that it is desirable to categorize as a regime. Training data sections in which the characteristics of a particular regime occur can be used as regime data for modules. The regime data can be an interval of the actual training data, or regime data can be training data that is modified as desired to better describe characteristics of a regime to be looked for. The regime data can also be constructed in some other way.

For example, suppose that fluid flow 10 is from an undersea well and that flow detector 12 makes measurements at 30 second intervals at the surface of the sea. Suppose sample data from fluid flow reveal three distinct patterns. In a first pattern, the sample data is characterized by high amplitude oscillation (HAO) and consists of triangular-shaped oscillations. A second data pattern is characterized by low amplitude oscillation (LAO) that consists of noisy oscillations at the same frequency superimposed on a stochastic time series. A third data pattern is a nondescript stochastic time series with no oscillation (NO).

To detect transitions between these regimes, each of expert module 14, expert module 15 and expert module 16 is provided with regime data from one of these distinct data patterns.

For example, regime data associated with expert module 14 is characterized by high amplitude oscillation (HAO) and consists of triangular-shaped oscillations with a period of approximately 30 samples. Regime data associated with expert module 15 is characterized by low amplitude oscillation (LAO) that consists of noisy oscillations at the same frequency superimposed on a stochastic time series. Regime data associated with expert module 16 is simply a nondescript stochastic time series with no oscillation (NO).

If new patterns appear in data from fluid flow 10, additional modules can be added that include regime data that is representative of the new patterns.

Within each module, some methodology is used to produce an association measure between the streaming data and the regime data. For example, expert module 14 may use adaptive filtering to generate an association measure between its regime data and the streaming data. However, if the period and shape of the triangular-shaped oscillations in the regime data change by small amounts unpredictably, a dynamical systems approach may be suited to calculate association measures. See Kriminger, Evan, et al., *Modified embedding for multi-regime detection in nonstationary streaming data*, ICASSP, 2011 IEEE international Conference, May 2011, pp. 2256-2259 for more information on how to use a dynamical systems approach to calculate an association measure.

Since stochastic time series are characterized by noisy and random processes, expert module 16 might use a linear adaptive filter to generate an associative measure. Since regime data associated with expert module 15 exhibits noisy oscillations that consist of both deterministic and random elements, expert module 15 might use a spectral feature to generate an association measure between its regime and streaming data. For example, a time-frequency method, such as a short-time Fourier transform (STFT), could be applied to the streaming data to extract a power spectrum value at the frequency of interest (the oscillation frequency) to be used as the spectral feature.

The system that detects a regime change in streaming data derived from fluid flow shown in FIG. 1 is just one example of how modules can be used to detect regime change in a data stream. There are many other applications for detection of regime change in a data stream.

Figure 2:
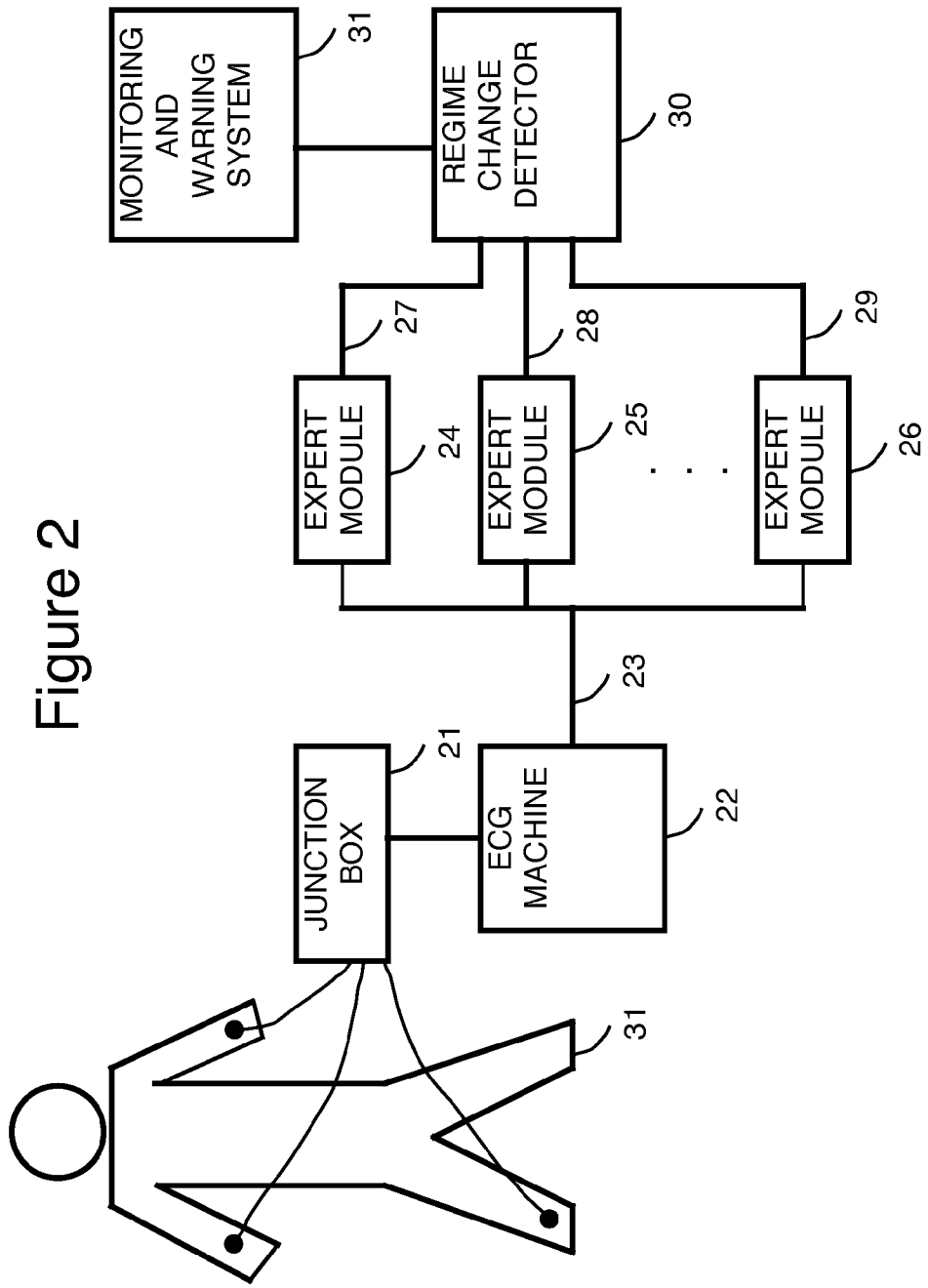
FIG. 2 is a simplified block diagram of a system that detects a regime change in streaming data derived an electrocardiogram machine in accordance with an implementation.

For example, FIG. 2 is a simplified block diagram of a system that detects a regime change in streaming data derived from an electrocardiogram (ECG). An ECG machine 22 utilizes a junction box 21 to gather electrical impulse information from a patient 31. ECG machine 22 produces streaming data on line 23 that represents results of the electrocardiogram. For example the streaming data may be in the form of an analog signal or a digital signal. In parallel, the streaming data is received by a plurality of modules. The plurality of modules is represented in FIG. 2 by an expert module 24, an expert module 25 and an expert module 26. While FIG. 2 shows three modules, this is only exemplary as the number of modules may be as low as two and as high as the number of regimes to be detected.

Each module has associated with it regime data. Each module compares its regime data with the streaming data. Based on the comparison, the module generates an association measure that indicates how closely characteristics of the streaming data resemble characteristics of the regime data associated with the module.

A regime change detector 30 receives an association measure from each of the modules. This is illustrated in FIG. 2 by regime change detector 30 receiving an association measure from expert module 24 over line a 27. Regime change detector 30 receives an association measure from expert module 25 over a line 28. Regime change detector 30 receives an association measure from expert module 26 over a line 29.

As the modules receive the streaming data, regime change detector 30 monitors the association measures generated by the modules. Change detector 30 determines from the association measures which regime currently best fits the characteristics of the streaming data.

When the association measures indicate there is a change in which regime currently best fits the characteristics of the streaming data, regime change detector 30 detects there has been a regime change. Regime change detector 30 signals a monitoring and warning system 31 that a regime change has occurred. Based on the new regime, monitoring and warning system 31 takes an appropriate predetermined action.

Different modules can calculate association measure in different ways. When different modules use different association measures calculated in different ways, it may be necessary to normalize the calculated association measures so that the association measure from each module can be accurately compared with each other. This can be done, for example, with normalized association values $Z_i$ as described in equation (1) above.

The system shown in FIG. 2 is used, for example, to detect beat types that may be identified from the ECG, including normal beats and a variety of irregularities such as premature ventricular contraction and atrial premature contractions. Real-time detection of these abnormal beats is potentially life-saving in a clinical setting, as beat irregularities are used to diagnose heart arrhythmias, myocardial infarctions, ventricular hypertrophy, and other health problems.

For example, if a patient has potentially 16 beat types, then regime data is obtained for each beat type and a separate module produces an association measure based on how closely characteristics of the streaming data resemble characteristics of the regime data associated with each module.

Figure 3:
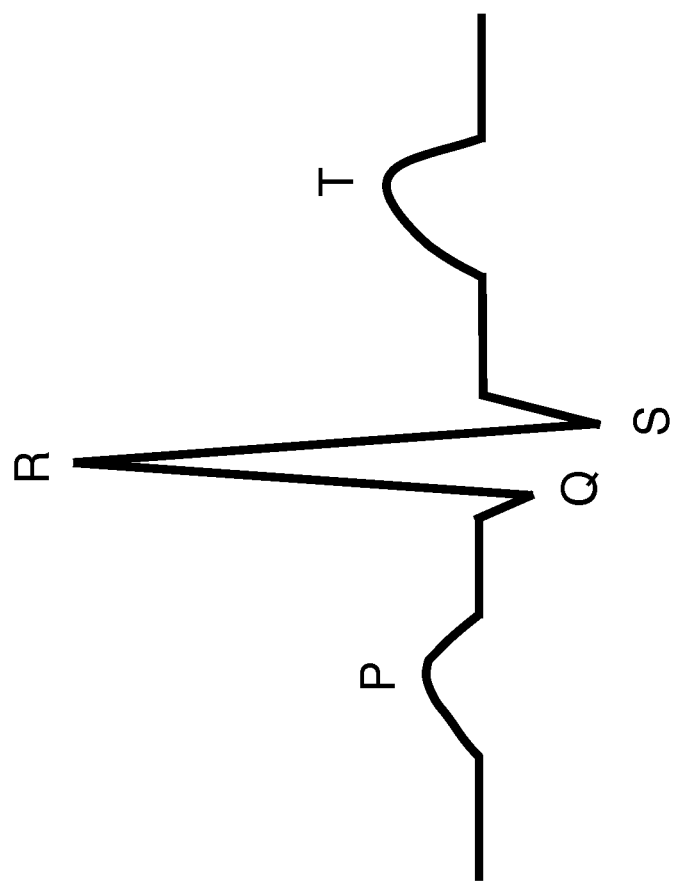
FIG. 3 shows a form of a typical electrocardiogram signal in accordance with the prior art.

Regime data for a new patient can be obtained from an ECG of the patient. FIG. 3 shows a form of a typical electrocardiogram signal with P, Q, R, S and T waves. When the patient has a type of beat not previously seen, new regime data can be generated from the ECG for the new type of beat and a new module can be created. An association measure to be used by the module is chosen, with the requirement that it be a scalar that is sufficiently descriptive of this beat type.

For example, when the module is associated with regime data representing ventricular flutter, the association measure may be the time between R waves of adjacent beats. R waves in an ECG signal are part of the QRS complex that result from ventricular contractions. The Euclidean distance between R waves, therefore, can be a very descriptive association measure when detecting ventricular flutter. The sample mean and standard deviation of the association measure is then stored and the Z-score can be calculated as described above in equation (1).

For example, the association measure for other modules might be Euclidean distance other features in P, Q, R, S and T waves of an ECG. The Euclidean distances can be transformed using equation (1) above into normalized Z scores. The module that produces the minimum absolute value Z-score is selected as the current regime.

FIG. 4 is a simplified flowchart that summarizes operation of a module. In a block 41, the module receives streaming data. In a block 42, the module compares a section of the streaming data to regime data to generate an association measure. As discussed above, the association measure could be calculated in a number of different ways, including use of Hamming distance, Euclidean distance, a likelihood ratio or another methodology that produces an association measure between the section of the streaming data and the regime data.

In an optional block 43, the association measure can be normalized. For example, equation (1) above can be used to normalize the association measure. Optionally the association measured can be normalized in some other way that will allow association measures from different modules to be fairly compared with each other. In a block 44, the normalized association measure is forward to a regime change detector. The regime change detector will monitor the normalized association measure from a number of modules to determine when a regime change has occurred.

The foregoing discussion discloses and describes merely exemplary methods and embodiments. As will be understood by those familiar with the art, the disclosed subject matter may be embodied in other specific forms without departing from the spirit or characteristics thereof. Accordingly, the present disclosure is intended to be illustrative, but not limiting, of the scope of the invention, which is set forth in the following claims.

We claim:

1. A system comprising:
   a processor;
   a plurality of processing programs executable on the processor to receive streaming data in parallel so that each processing program in the plurality of processing programs receives an identical copy of the streaming data, each respective processing program having corresponding regime data and to compare the streaming data with the regime data associated with the respective processing program to produce an association measure that provides a measure of similarity between the streaming data and the regime data associated with the respective processing program, wherein the regime data of the respective processing program defines characteristics of a regime for the respective processing program and each processing program in the plurality of processing programs has different regime data than regime data for all other processing programs in the plurality of processing programs, and wherein the plurality of processing programs are associated with respective different regimes, and wherein each regime of the different regimes corresponds to a pattern of behavior in the streaming data distinguished by dynamical or statistical properties of the streaming data; and
   a regime change detector to determine a regime change in the streaming data by comparing the association measure from the plurality of processing programs and identifying, based on the comparing of the association measures, which of the regimes best fits a characteristic of the streaming data.

2. The system of claim 1, wherein the processing programs are to normalize the association measures, wherein the comparing of the association measures comprises comparing the normalized association measures.

3. The system of claim 1, wherein each association measure is normalized according to $$Z_i = \frac{a_i - \mu_i}{\sigma_i}$$

where for a processing program i in the plurality of processing programs, $Z_i$ is a normalized association value that is generated from a non-normalized association value $a_i$, a mean $\mu_i$ and a standard deviation $\sigma_i$, where the mean $\mu_i$ and the standard deviation $\sigma_i$ are generated from a sampling distribution of non-normalized association values generated by the processing program i.

4. The system of claim 1, wherein the system is a fluid flow monitoring system, the system further comprising:
   a fluid flow measurement system to measure fluid flow through a conduit to produce the streaming data; and
   a warning system to warn a user in response to detecting the regime change.

5. The system of claim 1, wherein the system is an electrocardiogram system, the system further comprising:
   a heart monitor to monitor electrical signals generated by a human heart to produce the streaming data; and
   a warning system to warn a user in response to detecting the regime change.

6. The system of claim 5, wherein a first association measure produced by a first processing program is based on a time between electrocardiogram R waves of adjacent beats.

7. The system of claim 1, wherein the regime change detector is to categorize the streaming data as being in the regime that best fits the characteristic of the streaming data.

8. The system of claim 1, wherein the plurality of processing programs are to calculate the respective association measures using respective different measure calculation techniques.

9. The system of claim 8, where a first of the plurality of processing programs is to calculate a respective first association measure using adaptive filtering, and a second of the plurality of processing programs is to calculate a respective second association measure using a Fourier transform.

10. A method comprising:
sending streaming data in parallel to a plurality of modules so that each module in the plurality of modules receives an identical copy of the streaming data;
producing, by each respective module in the plurality of modules, an association measure, the association measure being a measure of similarity between the streaming data and regime data associated with the respective module producing the association measure, the regime data defining characteristics of a regime for the respective module, the plurality of modules associated with respective different regimes, wherein each module in the plurality of modules has different regime data than regime data for all other modules in the plurality of modules, and wherein each regime of the different regimes corresponds to a pattern of behavior in the streaming data distinguished by dynamical or statistical properties of the streaming data; and
determining, by a regime change detector, a regime change in the streaming data based on the association measures from the plurality of modules, wherein the determining comprises comparing the association measures from the plurality of modules, and identifying, based on the comparing, which of the regimes best fits the streaming data.

11. The method of claim 10, further comprising:
normalizing the association measures, wherein the comparing comprises comparing the normalized association measures.

12. The method of claim 10, further comprising:
normalizing the association measures according to $$Z_i = \frac{a_i - \mu_i}{\sigma_i}$$

where for a module i in the plurality of modules, $Z_i$ is a normalized association value that is generated from a non-normalized association value $a_i$, a mean $\mu_i$ and a standard deviation $\sigma_i$, where the mean $\mu_i$ and the standard deviation $\sigma_i$ are generated from a sampling distribution of non-normalized association values generated by the module i.

13. The method of claim 10, further comprising:
receiving the streaming data by a fluid flow monitoring system, the streaming data comprising measurement data of the fluid flow through a conduit; and
producing a warning signal to warn a user in response to detecting the regime change.

14. The method of claim 10, further comprising:
monitoring, by a heart monitor, electrical signals generated by a human heart in order to produce the streaming data; and
producing a warning signal to warn a user in response to detecting the regime change.

15. The method of claim 10, further comprising categorizing, by the regime change detector, the streaming data as being in the regime that best fits the characteristic of the streaming data.

16. The method of claim 10, where producing the association measures by the respective modules in the plurality of modules comprises using different measure calculation techniques in different ones of the plurality of modules.

17. Non-transitory computer readable media having computer readable instructions executable to cause a processor to:
send the streaming data in parallel to a plurality of modules so that each module in the plurality of modules receives an identical copy of the streaming data;
produce, by each respective module in the plurality of modules, an association measure, the association measure being a measure of similarity between the streaming data and regime data associated with the respective module producing the association measure, the regime data defining characteristics of a regime for the respective module, the plurality of modules associated with respective different regimes, wherein each module in the plurality of modules has different regime data than regime data for all other modules in the plurality of modules, and wherein each regime of the different regimes corresponds to a pattern of behavior in the streaming data distinguished by dynamical or statistical properties of the streaming data; and
determine a regime change in the streaming data based on comparing the association measures from the plurality of modules and identifying, based on the comparing, which of the regimes best fits a characteristic of the streaming data.

18. The non-transitory computer readable media of claim 17, wherein the association measures are normalized according to $$Z_i = \frac{a_i - \mu_i}{\sigma_i}$$

where for a module i in the plurality of modules, $Z_i$ is a normalized association value that is generated from a non-normalized association value $a_i$, a mean $\mu_i$ and a standard deviation $\sigma_i$, where the mean $\mu_i$ and the standard deviation $\sigma_i$ are generated from a sampling distribution of non-normalized association values generated by the module I, and
wherein the comparing comprises comparing the normalized association measures.

19. The non-transitory computer readable media of claim 17, wherein the computer readable instructions are executable to cause the processor to categorize the streaming data as being in the regime that best fits the characteristic of the streaming data.

20. The non-transitory computer readable media of claim 17, wherein the regime that best fits the characteristic of the streaming data is the regime associated with a highest association measure of the association measures.

* * * * *